United States Patent [19]
Olsen et al.

[11] Patent Number: 5,866,526
[45] Date of Patent: Feb. 2, 1999

[54] ENZYME PREPARATION COMPRISING A MODIFIED ENZYME

[75] Inventors: Arne Agerlin Olsen, Virum; Allan Svendsen, Birkerød; Kim Borch, Copenhagen K; Henrik Lund, Copenhagen N; Marianne Thellersen, Frederiksberg C, all of Denmark; Peter Rosholm, Pentaling Jaya, Malaysia; Niels Munk, Frederiksberg F, Denmark

[73] Assignee: Novo Nordisk A/S, Bagsvaerd, Denmark

[21] Appl. No.: 619,753

[22] PCT Filed: Oct. 4, 1994

[86] PCT No.: PCT/DK94/00368

§ 371 Date: May 2, 1996

§ 102(e) Date: May 2, 1996

[87] PCT Pub. No.: WO95/09909

PCT Pub. Date: Apr. 13, 1995

[30] Foreign Application Priority Data

Oct. 4, 1993 [DK] Denmark ................. 1111/93
Mar. 4, 1994 [DK] Denmark ................. 0259/94

[51] Int. Cl.⁶ .................................................. C11D 3/386
[52] U.S. Cl. .................... 510/392; 426/53; 426/54; 435/189; 435/198; 435/201; 435/202; 435/203; 435/204; 435/205; 435/209; 510/530
[58] Field of Search .............. 426/53, 54; 510/392, 510/383, 530; 435/189, 198, 201, 202, 203, 204, 205, 209

[56] References Cited

U.S. PATENT DOCUMENTS

| | | | |
|---|---|---|---|
| 5,047,332 | 9/1991 | Chahal | 426/53 X |
| 5,629,278 | 5/1997 | Baeck et al. | 510/530 X |
| 5,674,833 | 10/1997 | Milkelson et al. | 510/530 |
| 5,696,068 | 12/1997 | Outtrap et al. | 510/530 X |
| 5,707,950 | 1/1998 | Kastari et al. | 510/530 X |
| 5,719,115 | 2/1998 | Paatz et al. | 510/530 X |

FOREIGN PATENT DOCUMENTS

| | | |
|---|---|---|
| 0 149 520 | 7/1985 | European Pat. Off. . |
| 0 405 901 A1 | 1/1991 | European Pat. Off. . |
| WO 91/00345 | 1/1991 | WIPO . |
| WO 91/00910 | 1/1991 | WIPO . |
| WO 91/16424 | 10/1991 | WIPO . |
| WO 92/05249 | 4/1992 | WIPO . |
| WO 94/07998 | 4/1994 | WIPO . |

*Primary Examiner*—Michael Lusignan
*Attorney, Agent, or Firm*—Steve T. Zelson; Valeta Gregg

[57] ABSTRACT

An enzyme preparation comprising a modified enzyme selected from the group consisting of an amylase, lipase, oxidoreductase, pectinace or hemicellulase, the modified enzyme having an improved performance due to an alkaline pI and/or increased surface activity obtained by chemical modification or amino acid substitution, is useful e.g., in detergents, in baking flour, in animal feed, in the manufacture of cellulosic fabrics and for the treatment of lignocellulosic fibers.

23 Claims, 6 Drawing Sheets

ENZYME PREPARATION COMPRISING A MODIFIED ENZYME

CROSS-REFERENCE TO RELATED APPLICATIONS

This application is a 35 U.S.C. 371 national application of PCT/DK94/00368 filed Oct. 4, 1994, which is incorporated herein by reference.

FIELD OF INVENTION

The present invention relates to an enzyme preparation comprising a modified enzyme; a detergent additive and detergent composition containing the enzyme preparation; as well as use of the enzyme preparation e.g. in the pulp and paper industry, the textile industry, the juice industry, for beer brewing, for animal feed and for baking purposes.

BACKGROUND OF THE INVENTION

Enzymes have been used for a long time for a variety of industrial applications. For instance the use of enzymes in detergents, both laundry and dishwashing detergents, has become increasingly popular in recent years. Further important uses of enzymes are in papermaking pulp processing, in the baking industry for improving the properties of flour, in the wine and juice industries for the degradation of β-glucans, in the textile industry for bio-polishing of cellulosic fabrics such as viscose, i.e. for obtaining a soft and smooth fabric by subjecting the cellulosic fabrics to treatment by hemicellulolytic enzymes during their manufacture, and in animal feed for improving the digestibility of vegetable protein sources.

It is, however, far from easy to obtain an optimal enzyme performance e.g. in a detergent system, as the detergent formulation and washing conditions (for instance high pH, high ionic strength, and the inclusion of certain surfactants and builders) may have a crucial impact on the stability and activity of the enzyme.

Since washing conditions are quite often alkaline, some enzymes at least might be expected to show an improved performance if the pI of the enzymes is shifted to a value approximating that of the pH during application.

Similar considerations may apply to the use of enzymatic processes in other industries, e.g. one or more of the industries mentioned above.

E.g. when processing papermaking pulps, the lignocellulosic fibers may be subjected to enzymatic hydrolysis. Hydrolysing enzymes for fibre modification may be lipase for hydrolysis of triglycerides in pitch deposits, proteases for breakdown of structural proteins (e.g. extensin), and hemicellulase and pectinases for degradation of the carbohydrate material constituting the fibre wall.

It is well established that the effect e.g. of carbohydrases is limited due to electrostatic repulsion. So far no economical or technically feasible method for overcoming this limiting electrostatic repulsion has been suggested. In WO 93/11296 and WO 93/07332 it is described how the repulsion can be reduced by enzymatic removal of negatively charged glucuronic acid in the fibre matrix or by exchanging the counter ions on the acid groups in the fibre. These procedures are, however, very costly since bulk mass of lignocellulosic fibers must be treated with expensive specialty enzymes or metal salts. The latter may also cause problems in the internal water treatment of lignocellulosic fibre processing installations.

Furthermore, up till now it has been believed that the size of the enzyme molecules is another determining parameter for the effect of enzymes acting on lignocellulosic fibers. Average fibre pore sizes have been claimed to be of the same magnitude as the average diameter of the single enzyme molecules (Viikari, L., Kantelinen, A., Ratto, M. & Sundquist, J. (1991), Enzymes in Biomass Conversion, Chpt.2: Enzymes in Pulp and Paper Processing, p. 14, (Leatham, G. F. & Himmel, M. E., eds.). Thus, it is still an unsolved problem how to improve the effect of enzymatic hydrolysis of lignocellulosic fibers.

DESCRIPTION OF THE INVENTION

Surprisingly, it has been found that when lipases, amylases, oxidoreductases, pectinases and/or hemicellulases are derivatised in a way that masks the negatively charged side groups, this may lead to unexpected high increases in enzyme activity and/or in substrate availability. This is despite the fact that such a derivatisation increases the size of the enzyme molecules.

Thus, the electrostatic repulsion may be reduced through modification of the enzyme molecules in stead of modifying the substrate. Calculated in mass quantity, the amount of substrate is typically at least 100 times more than the mass of the enzyme product used in enzymatic processes, e.g. for treatment of the lignocellulosic fibers. Accordingly, it is much more economical to modify the enzyme instead of the lignocellulosic fibers.

The present invention relates to an enzyme preparation comprising a modified enzyme selected from the group consisting of amylases, lipases, oxidoreductases, pectinases and hemicellulases, said modified enzyme having an improved performance due to an alkaline pI and/or an increased surface activity obtained by chemical modification or amino acid substitution.

It is obvious that the enzyme preparation of the invention may contain one or more modified enzymes selected from the group consisting of amylases, lipases, oxidoreductases, pectinases and hemicellulases either alone or in combination with other enzymes which have not been subjected to a chemical modification or an amino acid substitution with the purpose of obtaining an alkaline pI and/or an increased surface activity.

In the present context, the term "improved performance" is intended to indicate that the modified enzyme, when subjected to the same standard test conditions as the parent enzyme, exhibits an improved effect compared to the parent enzyme. For enzymes intended to be included in detergent compositions, the modified enzyme is tested under standard washing conditions and its performance, e.g. with respect to removing stains and soiling, is compared to that of the non-modified parent enzyme. The wash performance of the modified enzyme may not only be evaluated under laundry conditions, but also under dishwashing conditions. For enzymes intended to be used in papermaking pulp processing, the performance of the modified enzyme on unbleached or oxygen bleached kraft pulp is evaluated from the amount of lignin that is dissolved from the pulp under a treatment with said endo-xylanase, subtracted the amount of lignin that is dissolved in a control treatment, where addition of endo-xylanase is omitted. The dissolved lignin is measured as the absorbance at 280 nanometers (Chpt. 5.1.4.2. by Lin, S. Y. in "Methods in Lignin Chemistry", Springer-Verlag, 1992), see example 6 below. A supplementary second parameter for measuring the effect of a treatment of kraft pulp with e.g. an endo-xylanase (a hemicellulase) is the content of residual lignin in the pulp. The best measure of the residual lignin content in the pulp is the kappa no. according to TAPPI procedure T236.

The isoelectric point, pI, is defined as the pH value at which the enzyme molecule is neutral, i.e. the sum of electrostatic charges (net electrostatic charge) is equal to zero. In this sum of course consideration of the positive or negative nature of the individual electrostatic charges must be taken into account. The pI may conveniently be determined experimentally by isoelectric focusing or by titrating a solution containing the enzyme.

The term "alkaline pI" is intended to indicate that the isoelectric point of the modified enzyme, as determined by isoelectric focusing under standard conditions, is higher than 7.5. According to the invention, it is generally preferred that the pI of the modified enzyme is at least 8.0, more preferably at least 8.5, most preferably at least 9.0. According to the invention, the pI of the modified enzyme should preferably be at least one pI unit, more preferably at least two pI units, most preferably at least three pI units, higher than that of the parent enzyme.

The parent lipase may suitably be a microbial lipase. As such, the parent lipase may be selected from yeast, e.g. Candida; lipases, bacterial, e.g. Pseudomonas or Bacillus, lipases; or fungal, e.g. Humicola or Rhizomucor, lipases. More specifically, suitable lipases may be the *Rhizomucor miehei* lipase (e.g. prepared as described in EP 238 023), *Thermomyces lanuginosa* lipase e.g. prepared as described in EP 305 216 (available from Novo Nordisk under the trade name Lipolase™), *Humicola insolens* lipase, *Pseudomonas stutzeri* lipase, *Pseudomonas cepacia* lipase, *Candida antarctica* lipase A or B, or lipases from rGPL, *Absidia blakesleena, Absidia corymbifera, Fusarium solani, Fusarium oxysporum, Penicillum cyclopium, Penicillum crustosum, Penicillum expansum, Rhodotorula glutinis, Thiarosporella phaseolina, Rhizopus microsporus, Sporobolomyces shibatanus, Aureobasidium pullulans, Hansenula anomala, Geotricum penicillatum, Lactobacillus curvatus, Brochothrix thermosohata, Coprinus cinerius, Trichoderma harzanium, Trichoderma reesei, Rhizopus japonicus* or *Pseudomonas plantari*. Other examples of suitable lipases may be variants of any one of the lipases mentioned above, e.g. as described in WO 92/05249 or WO 93/11254.

In a preferred embodiment of the invention, the degree of residual lipase activity is preferably above about 15%.

Examples of suitable amylases include *Bacillus amylases*, e.g. *Bacillus stearothermophilus* amylase, *Bacillus amyloliquefaciens* amylase, *Bacillus subtilis* amylase or *Bacillus licheniformis* amylase (e.g. as available from Novo Nordisk under the trade name Termamyl®), or Aspergillus amylases, e.g. *Aspergillus niger* or *Aspergillus oryzae* amylase. Other examples of suitable amylases may be variants of any one of the amylases mentioned above, e.g. as described in U.S. Pat. No. 5,093,257, EP 252 666, WO 91/00353, FR 2,676,456, EP 285 123, EP 525 610, PCT/DK93/00230.

The term "hemicellulase" is intended to include glycanases (apart from cellulose- and starch-degrading enzymes), mannanases, galactomannases, xylanases, arabinanases, polyglucuronases or polygalacturonases.

Examples of suitable xylanases include *Humicola insolens* (see e.g. WO 92/17573), *Bacillus pumilus* (see e.g. WO 92/03540), *Bacillus stearathermophilus* (see e.g. WO 91/18976, WO 91/10724), Bacillus sp. AC13 (see e.g. WO 94/01532), the genus Thermotoga (see e.g. WO 93/19171), the genus Rhodothermus (see e.g. WO 93/08275), the genus Dictyoglomus (see e.g. WO 92/18612), *Tricoderma longibrachiatum* and Chainia sp. (see e.g. EP 0 353 342 A1), *Thermoascus aurantiacus* (see e.g. U.S. Pat. No. 4,966,850), *Trichoderma harzianum* and *Trichoderma reseei* (see e.g. U.S. Pat. No. 4,725,544), *Aureobasidium pullulans* (see e.g. EP 0 373 107 A2), *Thermomyces lanuginosus* (see e.g. EP 0 456 033 A2), *Bacillus circulans* (WO 91/18978), *Aspergillus oryzae* (see e.g. SU 4610007), *Thermomonospora fusca* (see e.g. EP 0 473 545 A2), the genus Streptomyces (see e.g. U.S. Pat. No. 5,116,746), *Streptomyces lividans* (see e.g. WO 93/03155), *Streptomyces viridosporus* (see e.g. EP 496 671 A1), *Bacillus licheniformis* (see e.g. JP 9213868) and *Trichoderma longibrachiatum* [see W.J.J. van den Tweel et al.(Eds.), "Stability of Enzymes",Proceedings of an International Symposium heeld in Maastricht, The Netherlands, 22–25 Nov. 1992, Fisk, R. S. and Simpson, pp.323–328]. Other examples of suitable xylanases may be variants of any one of the xylanases mentioned above The term "oxidoreductases" is intended to include oxidases, laccases and peroxidases.

Examples of oxidoreductases include e.g. horseradish peroxidase, soybean peroxidase or a peroxidase derived from Coprinus, e.g. *C.cinereus*, or derived from Bacillus, e.g. *B. pumilus*. Other examples include lignin peroxidases and mangan peroxidases e.g. from *Phanerochaete chrysosporium*. Further examples include laccases from Trametes, e.g. *T. versicolor* or *T. villosa*, and laccases from *Polyporus pinsetus* or *Pyricularia oryzae*.

The term "pectinases" is intended to include polygalacturonases (EC3.2.1.15), pectinesterases (EC3.2.1.11), pectin lyases (EC4.2.2.10) and hemicellulases such as endo-1,3-β-xylosidase (EC 3.2.1.32), xylan 1,4-β-xylosidase (EC 3.2.1.37) and α-L-arabinofuranosidase (EC 3.2.1.55). A suitable source organism for pectinases may be *Aspergillus niger*.

It is to be understood that any of the enzymes mentioned in the present specification and claims may be produced by a given microorganism or, alternatively, may be a single (recombinant) enzyme, i.e. a component essentially free of other enzymes or enzyme activity usually occurring in an enzyme product produced by a given microorganism, the single enzyme being a recombinant enzyme, i.e. produced by cloning of a DNA sequence encoding the single enzyme and subsequent cell transformed with the DNA sequence and expressed in a host. The host is preferably a heterologous host, but the host may under certain conditions also be the homologous host.

The term "cellulosic fabric" is intended to include fabric originating from xylan-containing cellulose fibers, e.g. from wood pulp. Examples of cellulosic fabrics are viscose (rayon); Tencel®; all blends of viscose with other fabrics such as viscose/polyester blends, viscose/cotton blends, viscose/wool blends; flax (linen) and ramie and other fabrics based on xylan-containing cellulose fibers, including all blends of cellulosic fabrics with other fabrics such as cotton, wool, and polyester, e.g. viscose/polyester blends, viscose/cotton blends, viscose/wool blends, viscose/cotton/polyester blends, flax/cotton blends etc.

In a preferred embodiment of the enzyme preparation of the invention, the enzyme is chemically modified by coupling an amine ligand to the carboxyl group of glutamic acid or aspartic acid residues in the enzyme. By this chemical modification, the carboxylic acid groups are neutralized, thereby increasing the pI of the enzyme. The amine ligand is preferably an aminated sugar, aminated alcohol or aminated polyalcohol. Examples of suitable aminated sugars are glucosamine, isomeric forms thereof with the general formula $C_6H_{13}O_5N$, or oligomers and polymers of the general formula $[C_6H_{11}O_4N]_n$, for example polymers of glucosamines such as chitosans. Oligomers and polymers may be either branched or linear.

If an aminated alcohol is used for coupling to the carboxyl group, it should generally contain at least 3 carbon atoms. Examples of suitable aminated alcohols are aminopropanol or aminobutanol. More preferably the amine ligand is an aminated polyalcohol. Polyalcohols should generally contain at least 3 carbon atoms, and may for instance contain 6 carbon atoms. Examples of suitable aminated polyalcohols are glucamine, isomeric forms thereof with the general formula $C_6H_{15}O_5N$, or oligomers and polymers thereof with the general formula $[C_6H_{13}O_4N]_n$, wherein n>1.

Other suitable amine ligands are amine substituted alkanes and derivatives thereof. Preferred examples of amine substituted alkanes and their derivatives are amino acids such as lysine, polylysine; esters of amino acids; spermine; spermidine; putrescine; and the like.

The amine ligand such as an aminated sugar, alkane, alcohol or polyalcohol and polymer thereof, should have at least one amino group per monomeric unit, but should not be considered to be limited to having only one amino group per monomeric unit.

According to a preferred method, the coupling of the amine to the carboxyl group of glutamic acid or aspartic acid residues is mediated by a crosslinking agent capable of binding a carboxyl group and an amino group. The coupling reaction may suitably be carried out by standard methods as described by S. S. Wong, *Chemistry of Protein Conjugation and Cross-Linking*, CRC Press, Boca Raton, Fla., USA, 1991, in particular Chapter 2, IV, C, Chapter 4, IV and Chapter 5, II; or Wong and Wong, Enzyme Microb.Technol. 14, Nov. 1992, pp. 866–873. A particularly preferred crosslinking agent for the coupling reaction is a carbodiimide, e.g. 1-ethyl-3-(3-dimethylaminopropyl) carbodiimide (EDC).

Methods of conjugating proteins with ligands using EDC can be implemented according to manufacturer's description (e.g. Pierce Instructions 0475 C, 22980 X; 22981 X; EDC) using either the protocol for "Use of EDC for coupling of Haptens/small ligands to carrier Proteins" or "Protocol for Efficient Two-Step coupling of Proteins in Solution Using EDC and N-hydroxysuccinimide or sulfo-N-hydroxysucciminide".

For example the enzyme may be dissolved, or transferred by dialysis or desalting by size exclusion chromatography in a coupling buffer, such as, for instance 50 mM MES pH 5.0 containing 200 mM sodium chloride. The ligand, e.g. glucosamine, may be dissolved in coupling buffer as well. The conjugation reaction may proceed by mixing enzyme and ligand to a final concentration of 3 mg/ml for both enzyme and ligand followed by mixing with 5 mg of EDC per mg of enzyme. The conjugation reaction then runs for 2 hours at room temperature with continuous stirring. The reaction is terminated by removal of surplus reagent either by desalting by size exclusion chromatography or by extensive dialysis, e.g. against 0.2M ammonium acetate pH 6.9 at 5° C. The resulting derivative may then be stored at 5° C.

The degree of modification or incorporation of ligands may, of course, be controlled by adjustments in the initial enzyme, ligand and/or carbodiimide concentration. Variations in pH or temperature of the coupling buffer may also be included to optimise the conjugation reaction for a specific enzyme.

Naturally active site protection by substrate, substrate analogues and reversible inhibitors may be used to control of the modification reaction.

In another preferred embodiment of the enzyme preparation of the invention, the enzyme may be modified by substitution of one or more amino acids. The invention therefore further relates to an enzyme preparation comprising a modified enzyme selected from the group consisting of an amylase, lipase, oxidoreductase, pectinase or hemicellulase, wherein at least one negatively charged or neutral amino acid residue is substituted by a positively charged amino acid residue or, if the amino acid residue to be substituted is a negatively charged amino acid, a neutral amino acid residue. The object of said substitution is to provide a modified enzyme with an increased positive net charge relative to the parent enzyme, as a higher positive net charge results in a more alkaline pI.

When the parent enzyme is a lipase, the modified enzyme may be prepared by the general method described in WO 92/05249 (as well as described below). In describing a modified lipase according to the invention, the following nomenclature is used for ease of reference, using the conventional one-letter code for amino acid residues:

Original amino acid(s):position(s):substituted amino acid(s)

According to this nomenclature, for instance the substitution of arginine for aspartic acid in position 165 is shown as: D165R In one embodiment of a modified *T. lanuginosus* lipase, the electrostatic charge of the enzyme may be changed by substituting one or more amino acid residues located on the surface of the enzyme, in particular in one or more of the positions 5, 43, 45, 50, 69, 70, 72, 94, 102, 105, 165, 167, 199, 200 or 244, in combination with one or more of position 56, 87, 96, 210 or 254. More specifically, one or more amino acid residues may be substituted as follows:

D5R
E43Q
E45Q
T50K
L69R
D70R
T72K
N94K
D102K
S105K
D165R
D167R/K
T199K
N200R
T244K
In combination with
E56K/R
E87K/R;N/Q
D96K/R
E210K/R
D254K/R In a preferred embodiment the combination is /T72K/T244K/D102K/S105K/E87K/D96K/N94K/D165R/D167K/E43Q/E45 Q/T50K/L69R/D70R/.

In one embodiment of a modified *B. licheniformis* amylase, the electrostatic charge of the enzyme may be changed by substituting one or more amino acid residues located on the surface of the enzyme, in particular in one or more of the positions 53, 113, 114, 271, 419, 421 or 458. More specifically, one or more amino acid residues may be substituted as follows:

D53R/K
E113R/K
D114R/K
E271R/K
V419R/K
N421R/K
E447R/K
E458R/K
H471R/K

In one embodiment of a modified *T. lanuginosus* xylanase, the electrostatic charge of the enzyme may be changed by substituting one or more amino acid residues located on the surface of the enzyme, in particular in one or more of the positions 7, 11, 30, 95, 110, 127, 155, 156, 177, 181 or 183. More specifically, one or more amino acid residues may be substituted as follows:

E7R/K
E7T/S
E7Q/N
D11Q/N
D11R/K
E30R/K
N95R/K
D110R/K/S
D127K/R
N155R/K
A156R/K
Q177R/K
E181S/T
D183N/Q
D183R/K

In a further preferred embodiment of the enzyme preparation of the invention, the enzyme may be modified by substitution of at least one amino acid residue by at least one other amino acid residue to form an amino acid sequence specifying a glycosylation site recognized by a microorganism capable of glycosylating enzymes, such as a fungus or yeast. The object of introducing glycosylation site(s) is to provide a modified enzyme with an increased positive net charge or an increased hydrophilicity compared to that of the parent enzyme.

Preparation of modified enzymes by amino acid substitution

Several methods for introducing mutations into genes are known in the art. After a brief discussion of cloning enzyme-encoding DNA sequences, methods for generating mutations at specific sites within the enzyme-encoding sequence will be discussed.

Cloning a DNA sequence encoding an enzyme

The DNA sequence encoding a parent enzyme may be isolated from any cell or microorganism producing the enzyme in question by various methods, well known in the art. First a genomic DNA and/or cDNA library should be constructed using chromosomal DNA or messenger RNA from the organism that produces the enzyme to be studied. Then, if the amino acid sequence of the enzyme is known, homologous, labelled oligonucleotide probes may be synthesized and used to identify enzyme-encoding clones from a genomic library prepared from the organism in question. Alternatively, a labelled oligonucleotide probe containing sequences homologous to a known enzyme could be used as a probe to identify enzyme-encoding clones, using hybridization and washing conditions of lower stringency.

Yet another method for identifying enzyme-encoding clones would involve inserting fragments of genomic DNA into an expression vector, such as a plasmid, transforming enzyme-negative bacteria with the resulting genomic DNA library, and then plating the transformed bacteria onto agar containing a substrate for enzyme thereby allowing clones expressing the enzyme to be identified.

Alternatively, the DNA sequence encoding the enzyme may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *The EMBO J.* 3, 1984, pp. 801–805. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR) using specific primers, for instance as described in U.S. Pat. No. 4,683,202 or R. K. Saiki et al., *Science* 239, 1988, pp. 487–491.

Site-directed mutagenesis

Once an enzyme-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the enzyme-encoding sequence, is created in a vector carrying the enzyme gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984, Biotechnology 2:646–639). U.S. Pat. No. 4,760,025, by Estell et al., issued Jul. 26, 1988, discloses the introduction of oligo-nucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into enzyme-encoding DNA sequences is described in Nelson and Long, *Analytical Biochemistry* 180, 1989, pp. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Expression of modified enzymes

According to the invention, a mutated enzyme-encoding DNA sequence produced by methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a modified enzyme of the invention encoding may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding the enzyme variant of the invention, especially in a bacterial host, are the promoter of the lac operon of E.coli, the Streptomyces coelicolor agarase gene dagA promoters, the promoters of the Bacillus licheniformis α-amylase gene (amyL), the promoters of the Bacillus stearothermophilus maltogenic amylase gene (amym), the promoters of the Bacillus Amyloliquefaciens α-amylase (amyQ), the promoters of the Bacillus subtilis xylA and xylB genes etc. For transcription in a fungal host, examples of useful promoters are those derived from the gene encoding A. oryzae TAKA amylase, Rhizomucor miehei aspartic proteinase, A. niger neutral α-amylase, A. niger acid stable α-amylase, A. niger glucoamylase, Rhizomucor miehei lipase, A. oryzae alkaline protease, A. oryzae triose phosphate isomerase or A. nidulans acetamidase.

The expression vector of the invention may also comprise a suitable transcription terminator and, in eukaryotes, polyadenylation sequences operably connected to the DNA sequence encoding the enzyme variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from B.subtilis or B.licheniformis, or one which confers antibiotic resistance such as ampicillin, kanamycin, chloramphenicol or tetracyclin resistance. Furthermore, the vector may comprise Aspergillus selection markers such as amds, argB, niaD and sC, a marker giving rise to hygromycin resistance, or the selection may be accomplished by co-transformation, e.g. as described in WO 91/17243.

The procedures used to ligate the DNA construct of the invention encoding an enzyme variant, the promoter, terminator and other elements, respectively, and to insert them into suitable vectors containing the information necessary for replication, are well known to persons skilled in the art (cf., for instance, Sambrook et al. Molecular Cloning; A Laboratory Manual, CSH, NY, 1989).

The cell of the invention either comprising a DNA construct or an expression vector as defined above is advantageously used as a host cell in the recombinant production of an enzyme variant of the invention. The cell may be transformed with the DNA construct encoding the modified enzyme, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described below in connection with the different types of host cells.

The host cell may be a cell of a higher organism such as a mammal or an insect, but is preferably a microbial cell, e.g. a bacterial or a fungal (including yeast) cell.

Examples of suitable bacteria are gram-positive bacteria such as Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, or Streptomyces lividans or Streptomyces murinus, or gram-negative bacteria such as E.coli. The transformation of the bacteria may for instance be effected by protoplast transformation or by using competent cells in a manner known per se.

The yeast organism may favourably be selected from a species of Saccharomyces or Schizosaccharomyces, e.g. Saccharomyces cerevisiae. The filamentous fungus may advantageously belong to a species of Aspergillus, e.g. Aspergillus oryzae or Aspergillus niger. Fungal cells may be transformed by a process involving protoplast formation and transformation of the protoplasts followed by regeneration of the cell wall in a manner known per se. A suitable procedure for transformation of Aspergillus host cells is described in EP 238 023.

The modified enzyme may be produced by cultivating a host cell as described above under conditions conducive to the production of the modified enzyme and recovering the modified enzyme from the cells and/or culture medium.

The medium used to cultivate the cells may be any conventional medium suitable for growing the host cell in question and obtaining expression of the modified enzyme of the invention. Suitable media are available from commercial suppliers or may be prepared according to published recipes (e.g. in catalogues of the American Type Culture Collection).

The modified enzyme secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

Detergent Additives and Compositions

Due to their improved washing and/or dishwashing performance, modified amylases or lipases of the invention are particularly well suited for inclusion into detergent compositions, e.g. detergent compositions intended for performance in the range of pH 7–13, particularly the range of pH 8–11.

According to the invention, the modified amylase or lipase may be added as a component of a detergent composition. As such, it may be included in the detergent composition in the form of a detergent additive. The detergent composition as well as the detergent additive may additionally comprise one or more other enzymes conventionally used in detergents, such as proteases, oxidases, peroxidases and cellulases.

In a specific aspect, the invention provides a detergent additive. The modified amylase or lipase and optionally one or more other enzymes may be included in a detergent composition by adding separate additives containing one or more enzymes, or by adding a combined additive comprising all of these enzymes. A detergent additive of the invention, i.e. a separated additive or a combined additive, can be formulated e.g. as granulates, liquids, slurries, etc. Preferred detergent additive formulations are granulates, in particular non-dusting granulates, liquids, in particular stabilized liquids, slurries, or protected enzymes.

Non-dusting granulates may be produced, e.g. as disclosed in U.S. Pat. No. 4,106,991 and U.S. Pat. No. 4,661,452, and may optionally be coated by methods known in the art. The detergent enzymes may be mixed before or after granulation.

Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238 216.

In a still further aspect, the invention relates to a detergent composition comprising a modified amylase or lipase of the invention.

The detergent composition of the invention may be in any convenient form, e.g. as powder, granules or liquid. A liquid detergent may be aqueous, typically containing up to 90% of water and 0–20% of organic solvent, or non-aqueous, e.g. as described in EP Patent 120,659.

The detergent composition comprises a surfactant which may be anionic, non-ionic, cationic, amphoteric or a mixture of these types. The detergent will usually contain 0–50% of anionic surfactant such as linear alkylbenzene sulfonate, alpha-olefinsulfonate, alkyl sulfate, alcohol ethoxy sulfate or soap. It may also contain 0–40% of non-ionic surfactant such as nonyl phenol ethoxylate or alcohol ethoxylate. Furthermore, it may contain an N-(polyhydroxyalkyl)-fatty acid amide surfactant (e.g. as described in WO 92/06154).

The detergent may contain 1–40% of detergent builders such as zeolite, di or triphosphate, phosphonate, citrate, NTA, EDTA or DTPA, alkenyl succinic anhydride, or silicate, or it may be unbuilt (i.e. essentially free of a detergent builder).

The detergent composition of the invention may be stabilized using conventional stabilizing agents for the enzyme (s), e.g. a polyol such as e.g. propylene glycol, a sugar or sugar alcohol, lactic acid, boric acid, or a boric acid derivative, e.g. an aromatic borate ester, and the composition may be formulated as described in e.g. WO 92/19709 and WO 92/19708. Other enzyme stabilizers are well known in the art.

The detergent composition of the invention may contain bleaching agents, e.g. perborate, percarbonate and/or activator, tetraacetyl ethylene diamine, or nonanoyloxybenzene sulfonate, and may be formulated as described in e.g. WO 92/07057.

The detergent composition of the invention may also contain other conventional detergent ingredients, e.g. deflocculating polymers, fabric conditioners, foam boosters, foam depressors, anti-corrosion agents, soil-suspending agents, sequestering agents, anti-soil redeposition agents, dyes, bactericides, optical brighteners and perfumes as well as enzymes as mentioned above.

Particular forms of detergent composition within the scope of the invention and containing a modified amylase or lipase of the invention include:
a) A detergent composition formulated as a detergent powder containing phosphate builder, anionic surfactant, nonionic surfactant, silicate, alkali to adjust to desired pH in use, and neutral inorganic salt.
b) A detergent composition formulated as a detergent powder containing zeolite builder, anionic surfactant, nonionic surfactant, acrylic or equivalent polymer, silicate, alkali to adjust to desired pH in use, and neutral inorganic salt.
c) A detergent composition formulated as an aqueous detergent liquid comprising anionic surfactant, nonionic surfactant, organic acid, alkali, with a pH in use adjusted to a value between 7 and 11.
d) A detergent composition formulated as a nonaqueous detergent liquid comprising a liquid nonionic surfactant consisting essentially of linear alkoxylated primary alcohol, phosphate builder, alkali, with a pH in use adjusted to a value between about 7 and 11.
e) A compact detergent composition formulated as a detergent powder in the form of a granulate having a bulk density of at least 600 g/l, containing anionic surfactant and nonionic surf actant, phosphate builder, sodium silicate, and little or substantially no neutral inorganic salt.
f) A compact detergent composition formulated as a detergent powder in the form of a granulate having a bulk density of at least 600 g/l, containing anionic surfactant and nonionic surfactant, zeolite builder, sodium silicate, and little or substantially no neutral inorganic salt.
g) A detergent composition formulated as a detergent powder containing anionic surfactant, nonionic surfactant, acrylic polymer, fatty acid soap, sodium carbonate, sodium sulfate, clay particles, and sodium silicate.
h) A liquid compact detergent comprising 5–65% by weight of surfactant, 0–50% by weight of builder and 0–30% by weight of electrolyte.
i) A compact granular detergent comprising linear alkyl benzene sulphonate, tallow alkyl sulphate, C45 alkyl sulphate, $C_{4-5}$ alcohol 7 times ethoxylated, tallow alcohol 11 times ethoxylated, dispersant, silicone fluid, trisodium citrate, citric acid, zeolite, maleic acid acrylic acid copolymer, DETMPA, cellulase, protease, lipase, an amylolytic enzyme, sodium silicate, sodium sulphate, PVP, perborate and accelerator.
j) A granular detergent comprising sodium linear $C_{1-2}$ alkyl benzene sulfonate, sodium sulfate, zeolite A, sodium nitrilotriacetate, cellulase, PVP, TAED, boric acid, perborate and accelerator.
k) A liquid detergent comprising $C_{12-14}$ alkenyl succinic acid, citric acid monohydrate, sodium $C_{12-15}$ alkyl sulphate, sodium sulfate of $C_{12-15}$ alcohol 2 times ethoxylated, $C_{12-15}$ alcohol 7 times ethoxylated, $C_{12-15}$ alcohol 5 times ethoxylated, diethylene triamine penta (methylene phosphonic acid), oleic acid, ethanol, propanediol, protease, cellulase, PVP, suds supressor, NaOH, perborate and accelerator.

Furthermore, examples of suitable detergent compositions in which a modified amylase or lipase of the invention may advantageously be included comprises the detergent compositions described in EP 373 850, EP 378 261, WO 92/19709, EP 381 397, EP 486 073, WO 92/19707, EP 407 225, and WO 92/13054.

Dishwashing Compositions

Apart from a modified amylase or lipase of the invention, the dishwashing detergent composition comprises a surfactant which may be anionic, non-ionic, cationic, amphoteric or a mixture of these types. The detergent will contain 0–90% of non-ionic surfactant such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains 1–90% of detergent builders.

Examples of phosphorus-containing inorganic alkaline detergent builders, when present, include the water-soluble salts especially alkali metal pyrophosphates, orthophosphates, polyphosphates, and phosphonates. Examples of non-phosphorus-containing inorganic builders, when present, include water-soluble alkali metal carbonates, borates and silicates as well as the various types of water-insoluble crystalline or amorphous alumino silicates of which zeolites are the bestknown representatives.

Examples of suitable organic builders include the alkali metal, ammonium and substituted ammonium, citrates, succinates, malonates, fatty acid sulphonates, carboxymetoxy succinates, ammonium polyacetates, carboxylates, polycarboxylates, aminopolycarboxylates, polyacetyl carboxylates and polyhydroxsulphonates.

Other suitable organic builders include the higher molecular weight polymers and co-polymers known to have builder properties, for example appropriate polyacrylic acid, polymaleic and polyacrylic/polymaleic acid copolymers and their salts.

The dishwashing detergent composition may contain bleaching agents of the chlorine/bromine-type or the oxygen-type. Examples of inorganic chlorine/bromine-type bleaches are lithium, sodium or calcium hypochlorite and hypobromite as well as chlorinated trisodium phosphate. Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium. Hydantoin compounds are also suitable.

The oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED and glycerol triacetate.

The dishwashing detergent composition of the invention may be stabilized using conventional stabilizing agents for the enzyme(s), e.g. a polyol such as e.g.propylene glycol, a sugar or a sugar alcohol, lactic acid, boric acid, or a boric acid derivative, e.g. an aromatic borate ester.

The dishwashing detergent composition of the invention may also contain other conventional detergent ingredients, e.g. deflocculant material, filler material, foam depressors, anti-corrosion agents, soil-suspending agents, sequestering agents, anti-soil redeposition agents, dehydrating agents, yes, bactericides, fluorescers, thickeners and perfumes.

Other applications

It is contemplated that, dependent on the specificity of the enzyme, it may be employed for one or possibly more of the applications mentioned above, i.e. in the baking industry, in the wine and juice industry, for animal feed, and in paper-making pulp processing. In a particular embodiment, the enzyme preparation of the invention may comprise a combination of one or more enzymes selected from the group consisting of modified amylase, lipase and hemicellulase with one or more other enzymes.

Pulp and paper applications

In the papermaking pulp industry, the enzyme preparation according to the invention may be applied advantageously e.g. as follows:

For debarking, i.e. pretreatment with hydrolytic enzymes such as pectolytic and/or hemi-cellulolytic enzymes may degrade the pectin-rich cambium layer prior to debarking in mechanical drums resulting in advantageous energy savings.

For defibration (refining or beating), i.e. treatment of material containing cellulosic fibers with hydrolytic enzymes such as pectolytic and/or hemi-cellulolytic enzymes prior to the refining or beating which results in reduction of the energy consumption due to the hydrolysing effect of the enzymes on the surfaces of the fibers. Use of the enzyme preparation according to the present invention may result in higher energy savings as compared to use of unmodified enzymes, since the modified enzyme(s) possess a higher ability to penetrate fibre walls.

For fibre modification, i.e. improvement of fibre properties where partial hydrolysis across the fibre wall is needed which requires deeper penetrating enzymes (e.g. in order to make coarse fibers more flexible). Deep treatment of fibers has so far not been possible for high yield pulps e.g. mechanical pulps or mixtures of recycled pulps. This restriction has been ascribed to the nature of the fibre wall structure that prevents the passage of enzyme molecules due to physical restriction of the pore matrix of the fibre wall. Surprisingly, the modified (i.e. derivatised) enzymes of the enzyme preparation of the invention are more capable of penetrating into the fibre wall. This finding indicates that also for high yield pulps, the negatively charged acid groups on the micro fibrillar surfaces restrict the penetration of enzymes molecules by electrostatic repulsion.

For drainage: The drainability of papermaking pulps may be improved by treatment of the pulp with hydrolysing enzymes such as e.g. hemi-cellulases, lipase and/or pectinases. Use of the enzyme preparation according to the invention may be more effective, e.g. result in a higher degree of loosening bundles of strongly hydrated microfibrils in the fines fraction that limits the rate of drainage by blocking hollow spaces between the fibers and in the wire mesh of the paper machine.

For inter fibre bonding. Hydrolytic enzymes are applied in the manufacture of pulps for improving the inter fibre bonding. The enzymes rinse the fibre surfaces for noncellulosic impurities and fines, thus creating larger area of exposed cellulose and hemi-cellulose which improves the fibre-to-fibre hydrogen binding capacity. This process is also referred to as dehornification. Paper and board produced with a hemi-cellulase containing enzyme preparation according to the invention may have an improved strength or a reduced grammage, a smoother surface and an improved printability. This improvement is due to the improved penetrability of the modified/derivatised enzyme(s).

For enzymatic deinking. Partial hydrolysis of recycled paper upon pulping by use of hydrolysing enzymes such as e.g. lipase, pectinases, and hemi-cellulases are known to facilitate the removal and agglomeration of ink particles. Use of an enzyme preparation according to the invention may give a more effective loosening of ink from the surface structure due to a better penetration of the enzyme molecules into the fibrillar matrix of the fibre wall, thus softening the surface whereby ink particles are effectively loosened.

For bleaching of kraft pulp, see example 6 below. Treatment of oxygen bleached kraft pulp with endo-xylanase (a hemicellulase) is performed industrially for lowering the content of residual lignin in the pulp, thus reducing the need for chemicals in subsequent bleaching. To minimise the need for addition of mineral acid and to avoid problems with corrosion, it is required that the treatment with endoxylanase is performed at a high pH. However, partly due to electrostatic repulsion the performance of the majority of commercial endo-xylanase products is reduced as the pH is increased above 7.

The treatment of lignocellulosic pulp may, e.g., be performed as described in WO 93/08275, WO 91/02839 and WO 92/03608.

Textile applications

In another embodiment, the present invention relates to use of the enzyme preparation according to the present invention in the bio-polishing process. Bio-Polishing is a specific treatment of the yarn surface which improves fabric quality with respect to handle and appearance without loss of fabric wettability. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as e.g. desizing, scouring, bleaching, washing, dying/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. The preferred method of desizing is enzymatic hydrolysis of the size by the action of amylases. It is known that in order to achieve the effects of Bio-Polishing, a combination of enzymatic action and mechanical action is required. It is also known that if the enzymatic treatment is combined with a conventional treatment with softening agents, "super-softness" is achievable. It is contemplated that use of the enzyme preparation of the invention comprising amylase for enzymatic desizing is advantageous; and that use of the enzyme preparation of the invention comprising xylanase for bio-polishing of cellulosic fabrics, especially for viscose or Tencel® or blends thereof with other fabrics as mentioned above, is advantageous. Bio-polishing may be obtained by applying the method described e.g. in WO 93/20278.

Baking

In yet another embodiment, the present invention relates to use of the enzyme preparation according to the present invention, especially a chemically modified xylanase, amylase, lipase, laccase and/or oxidase preparation, in baking flour so as to improve the development, elasticity and/or stability of dough and/or the volume, crumb structure and/or anti-staling properties of the baked product. Although the enzyme preparation may be used for the preparation of dough or baked products prepared from any type of flour or meal (e.g. based on rye, barley, oat, or maize), the enzyme preparation of the invention have been found to be particularly useful in the preparation of dough or baked products made from wheat or comprising substantial amounts of wheat. The baked products produced with an enzyme preparation of the invention includes bread, rolls, baquettes and the like. For baking purposes the enzyme preparation of the invention may be used as having e.g. xylanase, lipase, amylase, oxidase or laccase as the only or major enzymatic activity, or may be used in combination with other enzymes such as a lipase, an amylase, an oxidase (e.g. glucose oxidase, peroxidase), a laccase and/or a protease; the lipase, amylase, oxidase and laccase optionally being modified as described herein.

Beer brewing

In yet another embodiment, the present invention relates to use of an enzyme preparation according to the invention in the beer brewing industry in particular to improve the filterability of wort e.g. containing barley and/or sorghum malt. The xylanase and/or amylase preparation may be used in the same manner as pentosanases conventionally used for brewing, e.g. as described by Vietor et al., 1993, J. Inst. Brew., May-June, 99, pp. 243–248, and EP 227 159. Furthermore, the xylanase preparation may be used for treatment of brewers spent grain, i.e. residuals from beer wort production containing barley or malted barley or other cereals, so as to improve the utilization of the residuals for, e.g., animal feed.

Juice etc.

In yet another embodiment, the present invention relates to use of an enzyme preparation according to the invention in the juice industry.

It is contemplated that the enzyme preparation of the invention, i.e. a xylanase preparation, is useful in the preparation of fruit or vegetable juice in order to increase yield, and in the enzymatic hydrolysis of various plant cell wall-derived materials or waste materials, e.g. from paper production, or agricultural residues such as wheat-straw, corn cobs, whole corn plants, nut shells, grass, vegetable hulls, bean hulls, spent grains, sugar beet pulp, and the like. The plant material may be degraded in order to improve different kinds of processing, facilitate purification or extraction of other component than the xylans like purification of beta-glucan or beta-glucan oligomers from cereals, improve the feed value, decrease the water binding capacity, improve the degradability in waste water plants, improve the conversion of e.g. grass and corn to ensilage, etc.

Finally, a xylanase preparation of the invention may be used in modifying the viscosity of plant cell wall derived material. For instance, the xylanases may be used to reduce the viscosity of feed containing xylan, to promote processing of viscous xylan containing material as in wheat separation, and to reduce viscosity in the brewing process.

Animal feed

In yet another embodiment, the present invention relates to use of an enzyme preparation according to the invention in animal feed (or for the treatment of animal feed prior to ingestion by the animal). The enzyme preparation is preferably added to the feed in an amount which is efficient for improving the digestibility of vegetable protein sources, e.g. cereals and legumes. Thus, e.g. a xylanase preparation of the present invention may be used for modification of animal feed and may exert its effect either in vitro (by modifying components of the feed) or in vivo. The xylanase preparation is particularly suited for addition to animal feed compositions containing high amounts of arabinoxylans and glucuronoxylans, e.g. feed containing cereals such as barley, wheat, rye or oats or maize. When added to feed the xylanase significantly improves the in vivo break-down of plant cell wall material partly due to a reduction of the intestinal viscosity (Bedford et al., Proceedings of the 1st symposium on Enzymes in Animal Nutrition, 1993, pp. 73–77), whereby a better utilization of the plant nutrients by the animal is achieved. Thereby, the growth rate and/or feed conversion ratio (i.e. the weight of ingested feed relative to weight gain) of the animal is improved.

The following examples further illustrate the present invention, and they are not intended to be in any way limiting to the scope of the invention as claimed.

EXAMPLE 1

Expression of *Humicola lanuginosa* lipase in *Aspergillus oryzae*:

Cloning of *Humicola lanuginosa* lipase and expression and characterization of the lipase in *Aspergillus oryzae* is described in EP application 305,216. The expression plasmid used is named p960.

The expression plasmid used in this application is identical to p960, except for minor modifications just 3' to the lipase coding region. The modifications were made the following way: p960 was digested with NruI and BamHI restriction enzymes. Between these two sites the BamHI/NheI fragment from plasmid pBR322, in which the NheI fragment was filled in with Klenow polymerase, was cloned, thereby creating plasmid pAO1 (FIG. 3), which contains unique BamHI and NheI sites. Between these unique sites BamHI/XbaI fragments from p960 was cloned to give pAHL (FIG. 4).

Site-directed in vitro mutagenisation of lipase gene:

The approach used for introducing mutations into the lipase gene is described in Nelson & Long, Analytical Biochemistry, 180, 147–151 (1989). It involves the 3-step generation of a PCR (polymerase chain reaction) fragment containing the desired mutation introduced by using a chemically synthesized DNA-strand as one of the primers in the PCR-reactions. From the PCR generated fragment, a DNA fragment carrying the mutation can be isolated by cleavage with restriction enzymes and re-inserted into the expression plasmid. This method is thoroughly described below. In FIGS. 5 and 6 the method is further outlined.

Construction of a plasmid expressing the D165R/D167K variant of *Humicola lanuginosa* lipase Linearization of plasmid pAHL:

The circular plasmid pAHL was linearized with the restriction enzyme SphI in the following 50 μl reaction mixture: 50 mM NaCl, 10 mM Tris-HCl, pH 7.9, 10 MM MgCl$_2$, 1 mM dithiothreitol, 1 μg plasmid and 2 units of SphI. The digestion was carried out for 2 hours at 37° C. The reaction mixture was extracted with phenol (equilibrated with Tris-HCl, pH 7.5) and precipitated by adding 2 volumes of ice-cold 96% ethanol. After centrifugation and drying of the pellet, the linearized DNA was dissolved in 50 μl H2O and the concentration estimated on an agarose gel.

3-step PCR mutagenesis:

As shown in FIG. 6, 3-step mutagenisation involves the use of four primers:

Mutagenisation primer (=A):
5'-CCATATGAAAACACTTTGATTCTATACCCATTTCC-3'
PCR Helper 1 (=B):
5'-GGTCATCCAGTCACTGAGACCCTCTACCTATTAAATCGGC-3'
PCR Helper 2 (=C):
5'-CCATGGCTTTCACGGTGTCT-3'
PCR Handle (=D):
5'-GGTCATCCAGTCACTGAGAC-3'

Helper 1 and helper 2 are complementary to sequences outside the coding region, and can thus be used in combination with any mutagenisation primer in the construction of a mutant sequence.

All 3 steps were carried out in the following buffer containing: 10 mM Tris-HCl, pH 8.3, 50 mM KCl, 1.5 mM MgCl$_2$, 0.001% gelatin, 0.2 mM DATP, 0.2 mM dCTP, 0.2 mM dGTP, 0.2 mM TTP, 2.5 units Taq polymerase.

In step 1, 100 pmol primer A, 100 pmol primer B and 1 fmol linearized plasmid was added to a total of 100 μl reaction mixture and 15 cycles consisting of 2 minutes at 95° C., 2 minutes at 37° C. and 3 minutes at 72° C. were carried out.

The concentration of the PCR product was estimated on an agarose gel. Then, step 2 was carried out. 0.6 pmol step 1 product and 1 fmol linearized plasmid was contained in a total of 100 μl of the previously mentioned buffer and 1 cycle consisting of 5 minutes at 95° C., 2 minutes at 37° C. and 10 minutes at 72° C. was carried out.

To the step 2 reaction mixture, 100 pmol primer C and 100 pmol primer D is added (1 μl of each) and 20 cycles consisting of 2 minutes at 95° C., 2 minutes at 37° C. and 3 minutes at 72° C. were carried out. This manipulation comprised step 3 in the mutagenisation procedure.

Isolation of mutated restriction fragment:

The product from step 3 was isolated from an agarose gel and re-dissolved in 20 μl H$_2$O. Then, it was digested with the restriction enzymes BamHI and BstXI in a total volume of 50 μl with the following composition: 100 mM NaCl, 50 mM Tris-HCl, pH 7.9, 10 mM MgCl$_2$, 1 mM DTT, 10 units of BamHI and 10 units of BstXI. Incubation was at 37° C. for 2 hours. The 733 bp BamHI/BstXI fragment was isolated from an agarose gel.

Ligation to expression vector pAHL:

The expression plasmid pAHL was cleaved with BamHI and BstXI under conditions indicated above and the large fragment was isolated from an agarose gel. To this vector, the mutated fragment isolated above was ligated and the ligation mix was used to transform *E.coli*. The presence and orientation of the fragment was verified by cleavage of a plasmid preparation from a transformant with restriction enzymes. Sequence analysis was carried out on the double-stranded plasmid using the DyeDeoxy™ Terminater Cycle Sequencing Kit (Applied Biosystems) on an ABI DNA sequencer, model 373A. The plasmid was named pAHLD165R/D167K and is identical to pAHL, except for the substituted codons.

EXAMPLE 2

Primers used for the construction of other Humicola lipase variants.

The following mutations were incorporated using the same method as described in example 1. The primers used for the modifications are listed below.

| Mutations | Primer A sequence |
|---|---|
| E87K/D96K/D102K | 5'-GCCGGAGCAAATCTTATTTATTTCTTTCAACTTG A A G T T A A G - ATTCCCGATCCAGTTTTTTATGGAACGAGA-3' |
| E210K | 5'-GCTGTAACCGAACTTGCGCGGCGGGAG-3' |
| T199K/N200R | 5'-AGGGACAATATCCCTCTTGTGGGTAATGCG-3' |

EXAMPLE 3

Construction of plasmids expressing combination variants of Humicola lipase.

The plasmids pAHLD165R/D167K/D102K/D96K/E87K,
pAHLD165R/D167K/D102K/D96K/E87K/E210K
pAHLD165R/D167K/D102K/D96K/E87K/T199K/N200R
pAHLD165R/D167K/D102K/D96K/E87K/T199K/N200R/E210K
were constructed by performing successive mutagenisation steps using the appropriate primers.

EXAMPLE 4

Expression of lipase variants in Aspergillus Transformation of *Aspergillus oryzae* (general procedure).

100 ml of YPD (Sherman et al., Methods in Yeast Genetics, Cold Spring Harbor Laboratory, 1981) was inoculated with spores of A. oryzae and incubated with shaking for about 24 hours. The mycelium was harvested by filtration through miracloth and washed with 200 ml of 0.6M MgSO$_4$. The mycelium was suspended in 15 ml of 1.2M MgSO$_4$, 10 mM NaH$_2$PO$_4$, pH=5.8. The suspension was cooled on ice and 1 ml of buffer containing 120 mg of Novozym® 234, batch 1687 was added. After 5 min., 1 ml of 12 mg/ml BSA (Sigma type H25) was added and incubation with gentle agitation continued for 1.5–2.5 hours at 37° C. until a large number of protoplasts was visible in a sample inspected under the microscope.

The suspension was filtered through miracloth, the filtrate transferred to a sterile tube and overlayed with 5 ml of 0.6M sorbitol, 100 mM Tris-HCl, pH=7.0. Centrifugation was performed for 15 min. at 1000 g and the protoplasts were collected from the top of the MgSO$_4$ cushion. 2 volumes of STC (1.2M sorbitol, 10 mM Tris-HCl, pH=7.5, 10 mM CaCl$_2$) were added to the protoplast suspension and the mixture was centrifuged for 5 min. at 1000 g. The protoplast pellet was resuspended in 3 ml of STC and repelleted. This was repeated. Finally, the protoplasts were resuspended in 0.2–1 ml of STC. 100 µl of protoplast suspension was mixed with 5–25 µg of p3SR2 (an A. nidulans amds gene carrying plasmid described in Hynes et al., Mol. and Cel. Biol., Vol. 3, No. 8, 1430–1439, Aug. 1983) in 10 µl of STC. The mixture was left at room temperature for 25 min. 0.2 ml of 60% PEG 4000 (BDH 29576), 10 mM CaCl$_2$ and 10 mM Tris-HCl, pH=7.5 was added and carefully mixed (twice) and finally 0.85 ml of the same solution was added and carefully mixed. The mixture was left at room temperature for 25 min., spun at 2.500 g for 15 min. and the pellet was resuspended in 2 ml of 1.2M sorbitol. After one more sedimentation the protoplasts were spread on minimal plates (Cove, Biochem. Biophys. Acta 113 (1966) 51–56) containing 1.0M sucrose, pH=7.0, 10 mM acetamide as nitrogen source and 20 mM CsCl to inhibit background growth. After incubation for 4–7 days at 37° C. spores were picked, suspended in sterile water and spread for single colonies. This procedure was repeated and spores of a single colony after the second reisolation were stored as a defined transformant.

EXAMPLE 5

Expression of lipase variants in A. oryzae

The plasmids described above were transformed into A. oryzae IFO 4177 by cotransformation with p3SR2 containing the amds gene from A. nidulans as described in the above example. Protoplasts prepared as described were incubated with a mixture of equal amounts of expression plasmid and p3SR2, approximately 5 µg of each were used. Transformants which could use acetamide as sole nitrogen source were reisolated twice. After growth on YPD for three days, culture supernatants were analyzed using an assay for lipase activity. The best transformant was selected for further studies and grown in a 1 l shake-flask on 200 ml FG4 medium (3% soy meal, 3% maltodextrin, 1% peptone, pH adjusted to 7.0 with 4M NaOH) for 4 days at 30° C.

EXAMPLE 6 pI values of Lipolase and variants thereof

The theoretical pI values of Lipolase and modifications thereof have been determined based on the sequence numbers of titratable groups in the residues Asp (D), Glu (E), Lys(K), Arg(R), His(H) and Tyr (Y) within the pH range 1–14.

The pI values are listed below:

| | |
|---|---|
| Lipase wild-type (Lipolase) | pI 4.7 |
| +D165R/D167K/D102K/D96K/EB7K | pI 7.6 |
| +D165R/D167K/D102K/D96K/E87K/E210K | pI 8.1 |
| +D165R/D167K/D102K/D96K/E87K/T199K/N200R | pI 8.2 |
| +D165R/D167K/D102K/D96K/E87K/T199K/N200R/E210K | pI 8.5 |

EXAMPLE 7A

Conjugation of Lipolase™ with glucosamine, polylysine and polyarginine, respectively, mediated by EDC Conjugation of Lipolase™ (a lipase expressed in and produced by Aspergillus oryzae; produced and sold by Novo Nordisk A/S, Bagsvaerd, Denmark) with glucosamine, polylysine and polyarginine, respectively, through carbodiimide mediated coupling was performed according to standard procedures.

An enzyme stock solution was prepared by dissolving approximately 50 mg/ml of highly purified Lipolase™ in 50 mM boric acid/NaOH at pH 9.0. The enzyme was diluted in coupling buffer (50 mM MES pH 5.0 containing 200 mM sodium chloride). The glucosamine, polylysine (MW 8200) and polyarginine (MW 6000), respectively, was dissolved in coupling buffer as well.

The conjugation reaction proceeded by mixing enzyme and polylysine/polyarginine to a final concentration of 3 mg/ml for both enzyme and glucosamine followed by addition to 5 mg of EDC per mg of enzyme to mediate the reaction. The conjugation reaction continued for 2 hours at room temperature with continuos magnetic stirring.

The reaction was terminated by removing surplus reagent by extensive dialysis against 0.1M ammonium hydrogencarbonate pH 8 at 5° C. (for polylysine and polyarginine) and agains 0.2M ammonium acetate pH 6.9 at 5° C. (for glucosamine). The derivative was stored at 5° C.

The prepared Lipolase™-glucosamine derivative has a pI value of 9.5 as determined by isoelectric focusing and 21.7% residual Lipolase™ activity when compared to wild-type Lipolase™. The prepared Lipolase™-polylysine derivative has a pI value of 9.5 as determined by isoelectric focusing and 47.9% residual Lipolase™ activity when compared to wild-type Lipolase™. The prepared Lipolase™-polyarginine derivative has a pI value of 9.5 as determined by isoelectric focusing and 27.1% residual Lipolase™ activity when compared to wild-type Lipolase™.

The activity was measured according to the standard Novo Nordisk Lipolase method AF-95-GB (available from Novo Nordisk A/S on request) which is hereby incorporated by reference.

EXAMPLE 7B

Conjugation of Termamyl® with glucosamine mediated by EDC

Conjugation of Termamyl® (an amylase expressed in and produced by a strain of Bacillus licheniformis, produced and sold by Novo Nordisk A/S, Bagsvaerd, Denmark) with glucosamine through carbodiimide mediated coupling was performed according to standard procedures.

An enzyme stock solution was prepared by dissolving approximately 50 mg/ml of highly purified Termamyl™ in Britton-Robinson buffer at pH 9 (0.04M phosphoric acid, acetic acid, boric acid; adjustment of pH by titration with 0.2N NaOH). The enzyme was diluted in coupling buffer (50 mM MES pH 5.0 containing 200 mM sodium chloride). The glucosamine was dissolved in coupling buffer as well.

The conjugation reaction proceeded by mixing enzyme and glucosamine to a final concentration of 3 mg/ml for the enzyme and 3, 0.6 and 0,3 mg/ml of glucosamine followed by addition to 5 mg of EDC per mg of glucosamine. The conjugation reactions continued for 2 hours at room temperature with continuous magnetic stirring.

The reaction was terminated by removing surplus reagent by extensive dialysis towards 0.2M ammonium acetate pH 6.9 at 5° C. The derivatives were stored at 5° C.

The amylase activity is determined by the standard Novo Nordisk method AF-124-GB (available from Novo Nordisk A/S on request) for determination of amylase activity in Termamyl® preparations. The method is hereby incorporated by reference.

The following variants were prepared:

| | TERMAMYL | Glucos-amino | Amylase activity | pI |
|---|---|---|---|---|
| Derivative #1 | 3 mg/ml | 3 mg/ml | 3.90 KNU/ml | 9.5 |
| Derivative #2 | 3 mg/ml | 3 mg/ml | 8.80 KNU/ml | 9–9.5 |
| Derivative #3 | 3 mg/ml | 3 mg/ml | 15.40 KNU/ml | 8.5–9 |

EXAMPLE 7C

Conjugation of Termamyl® with glucosamine mediated by EDC at pH 6

Conjugation of Termamyl® (an amylase expressed in and produced by a strain of *Bacillus licheniformis*) with the glucosamine through carbodiimide mediated coupling is performed according to standard procedures.

An enzyme stock solution was prepared by dissolving approximately 50 mg/ml of highly purified Termamyl® in Britton-Robinson buffer at pH 9 (0,04M phosphoric acid, acetic acid, boric acid; adjustment of pH by titration with 0.2N NaOH). The enzyme was diluted in coupling buffer (50 mM MES pH 6.0 containing 200 mM sodium chloride). The glucosamine was dissolved in coupling buffer as well.

The conjugation reaction proceeded by mixing enzyme and glucosamine to a final concentration of 3 mg/ml for the enzyme and of 3 and 1,5 mg/ml of glucosamine followed by addition to 5 mg of EDC per mg of glucosamination. The conjugation reactions continued for 2 hours at room temperature with continuous magnetic stirring.

The reaction was terminated by removing surplus reagent by extensive dialysis towards 0.2M ammonium acetate pH 6.9 at 5° C. The derivatives were stored at 5° C.

The amylase activity is determined by the standard Novo Nordisk method AF-124-GB (available from Novo Nordisk A/S on request) for determination of amylase activity in Termamyl® preparations. The method is hereby incorporated by reference.

The following variants were prepared:

| | TERMAMYL | Glucos-amino | Amylase activity | pI |
|---|---|---|---|---|
| Derivative #5 | 3 mg/ml | 3 mg/ml | 10.1 KNU/ml | 8–9 |
| Derivative #6 | 3 mg/ml | 1.5 mg/ml | 15.3 KNU/ml | 7.5–8.5 |

EXAMPLE 7D

Conjugation of *Thermomyces lanuginosus* xylanase with glucosamine mediated by EDC Conjugation of *Thermomyces lanuginosus* xylanase with glucosamine through carbodiimide mediated coupling was performed according to standard procedures.

An enzyme stock solution was prepared by dialysis against coupling buffer for equilibration. The enzyme was diluted in coupling buffer (50 mM MES pH 5.0 containing 200 mM sodium chloride). The glucosamine was dissolved in coupling buffer as well.

The conjugation reaction proceeded by mixing enzyme and glucosamine to a final concentration of 2 mg/ml for both enzyme and glucosamine followed by addition to 5 mg of EDC per mg of enzyme to mediate the reaction. The conjugation reaction continued for 2 hours at room temperature with continuos magnetic stirring.

The reaction was terminated by removing surplus reagent by extensive dialysis against Britton-Robinson buffer (see Example 1B) at pH 7 at 5° C. The derivative was stored at 5° C.

The xylanase-glucosamine derivative prepared according to the above described procedure was shown to be monomeric by size-exclusion chromatography on a TSK-G2000SW column, has a pI value of 9 as determined by isolectric focusing and 3.8% residual xylanase activity when compared to wild-type *T. lanuginosus* xylanase. The activity is measured according to the standard Novo Nordisk xylanase method AF-293.9/1-GB (available from Novo Nordisk A/S on request) which is hereby incorporated by reference.

EXAMPLE 8

Interfacial activity of Lipolase and the glucosamine derivative thereof

By means of tensiometry it was shown that glucosamination of Lipolase™ results in a significant increase in the interfacial activity of the enzyme at alkaline pH values.

The measurements were performed with a Sigma 70 tensiometer from KSV, Finland, equipped with a Wilhelmy Pt-plate. The experiments were carried out by injecting 25 $\mu$l highly purified enzyme (adjusted to $OD_{280\ nm}$=1.66 for both Lipolase™ and the glucosamine derivative ("Lipolase-GA") into a 100 ml buffer-solution, while following the surface tension $\gamma$ with time.

Measurements were performed at 25° C. in 50 mM Tris pH 7+500 mM NaCl and 50 mM glycine pH10+500 mM NaCl. Addition of an excess of neutral salt was done in order to increase the adsorption of enzyme at the air-water interface.

Already at pH 7 it appears that the extent of adsorption is increased by the glucosamination (FIG. 1). Going from pH 7 to pH 10 does not in any major way alter the adsorption of native Lipolase™. On the other hand, the pI of the enzyme derivative resulted in a significant increase in its surface activity (FIG. 2).

EXAMPLE 9

Improved lipolytic performance in the presence of alcohol ethoxylates

Using a monolayer equipment (KSV-5000, KSV Instruments, Finland) it was demonstrated that glucosamination of Lipolase™ considerably increased the lipolytic action of this lipase in the presence of long-chain alcohol ethoxylates. A large number of non-ionic surfactants present in most currently used detergents are alcohol ethoxylates (e.g. Dobanol 25–7).

Experimental

A mixed monolayer of a well-defined overall composition, made up of a diglyceride substrate and a monocomponent alcohol ethoxylate was spread on an aqueous subphase. The surface pressure was adjusted to the desired value, and a well-defined amount of lipase was injected into the subphase. Lipolytic action is manifested through the speed of a mobile barrier compressing the monolayer in order to maintain constant surface pressure as insoluble substrate molecules are hydrolysed into more water soluble reaction products. Using this assay, lipases are discriminated by:

B: The final area-fraction of substrate left unhydrolysed by the lipase.

The table below illustrates that the glucosamine and polylysine derivatives of Lipolase™, respectively, performs considerably better in the presence of alcohol ethoxylates. In addition it is demonstrated that the performance of lipase in the presence of alcohol ethoxylates is increased when the net charge of the lipase is increased.

Improved tolerance of Lipolase™ towards alcohol ethoxylates upon glucosamination

| Enzyme | β |
|---|---|
| Lipolase™ (wild-type) | 59% |
| Wild-type + E210R | 56% |
| Wild-type + T199K/N200R | 53% |
| Wild-type + D102K/S105K | 49% |
| Glucosaminated derivative | 0% |
| Polylysine derivative | 0% |

Note: 10 mM glycine buffer, substrate: Dicaprin, 10 Lipase Units (LU), pH 10.0, 25° C., 30 mN/m. Additive: Heptaethylene monooctadecyl ether

EXAMPLE 10

Washing performance of amylase and glucosamine derivative thereof
Fabric with coloured starch In order to visualize the detergency of the enzyme preparation of the invention, coloured starch was produced according to the following procedure. 50 g of potato starch was solubilized in 500 ml $H_2O$ and heated to 80° C. Then 5 g of the dye Cibacron Blue 3GA was added together with 100 g sodium sulphate and 500 ml deionized water. The mixture was heated for 15 minutes. Subsequently 5 g trisodiumphosphate was added, the temperature was lowered to 50° C. and the mixture was agitated for 75 minutes and then cooled to room temperature. A centrifuging step was applied to remove surplus of unreacted dye.

100% cotton fabric was then submerged into the solution, pressed through a roller and line dryed. The remission of the fabric at 660 nm was then measured and should be in the range of 35–45.
Washing procedure Swatches of the dyed fabric were washed in glass beakers with agitation by a magnetic stirrer.
Volume: 60 ml
Wash time: 20 min
Rinse: 15 min
Swatches: 6 swatches with a diameter of 2.5 cm
Temperature: 55° C.
Detergent: Commercial high-pH European automatic dishwashing detergent, 3 g/l
pH: 10.2
Drying: Line drying
Repetitions: 1
Enzymes
Termamyl™
Glucosaminated Termamyl® (TRMEDC1), see Example 7B Evaluation The starch removal on the swatches are measured in respect to remission at 660 nm, once on both sides. (Apparatus: Elrepho from Data Color/Switzerland).

Data R and standard deviations ( ).

| Enzyme | 0 KNU/l | 0.4 KNU/l | 1.0 KNU/l | 3.0 KNU/l |
|---|---|---|---|---|
| Termamyl | 53.65 | 68.55 | 76.40 | 82.86 |
|  | (1.04) | (0.34) | (0.59) | (0.12) |
| TRMEDC1 | 53.65 | 73.50 | 82.33 | 86.20 |
|  | (1.04) | (0.58) | (0.24) | (0.15) |

The results demonstrate that the glucosaminated enzyme performs significantly better than than non-modified Termamyl®.

EXAMPLE 11

Improved performance of Lipolase™ in the presence of detergents

High pI derivatives of Lipolase™ were prepared as described in example 7A. Dervatisation of Lipolase™ was carried out at a ratio of Lipolase to polylysine/polyarginine of 1:1, based on weight.
EDC3: Lipolase™ conjugated with glucosamine
EDC10: Lipolase™ conjugated with poly-L-arginine (6.0 kDa, Sigma P4663)
EDC11: Lipolase™ conjugated with poly-L-lysine (8.2 kDa, Sigma P6516)

The high pI of the derivatives were confirmed by IEF. Samples were loaded onto an Ampholine PAG-plate pH 3.5–9.5 (Pharmacia) and run according to the manufacturer's instructions. The three conjugates were shown to have a pI above 9.5.

The residual activities of the conjugates were measured using the standard Novo Nordisk Lipolase™ method AF-95-GB which is available from Novo Nordisk A/S upon request.

The residual activities of the Lipolase derivatives are shown in the table below:

| Enzyme | $A_{280}$ | LU/ml | $LU/A_{208}$ | Residual activity (%) |
|---|---|---|---|---|
| Lipolase | 1.0 | 4077 | 4077 | 100 |
| EDC3 | 1.61 | 1300 | 813 | 20 |
| EDC10 | 0.41 | 727 | 1773 | 43 |
| EDC11 | 0.57 | 811 | 1423 | 35 |

The performance of the Lipolase conjugates in the presence of detergents were investigated in an assay using paranitrophenyl palmitate (pNP-palmitate, Sigma N2752) as a substrate. The absorbance of the p-nitrophenol released upon lipase catalused hydrolysis was measured at 405 nm as a function of time. The assay was run in 0.1M Tris-HCl, 0.352 mM $CaCl_2$, pH 10, containing either Dobanol 25–7 (nonionic detergent) or Ariel Ultra (full laundry detergent, commercial available from the company Procter & Gamble; enzymatic activities removed by heating). Lipolase and derivatives thereof were dosed on an activity bases (3.75 LU/ml).

The results are shown in the table below.

The results demonstrate that the high pI conjugates have considerable higher activity.

The improvement factor IF in the table, defined as $$IF = (\Delta A_{405} \text{derivative})/(\Delta A_{405} \text{wild-type})$$

after 30 minutes, expresses the amount of lipase variant protein needed to obtain the same effect as that obtained with the reference wild-type lipase.

| Enzyme | Description | Dosage | IF Dobanol 25-7 (4 μg/ml) | IF Ariel Ultra (100 μg/ml) |
| --- | --- | --- | --- | --- |
| Lipolase | Wild-type | 3.75 LU/ml | 1.0 | 1.0 |
| poly-Arg | WT + p-Arg (control) | 2.1 μg/ml | 1.0 | 1.0 |
| poly-Lys | WT + p-Lys (control) | 2.6 μg/ml | 0.5 | 0.8 |
| glucosamine | WT + glucosamine | 12.5 mM | 0.7 | n.a. |
| EDC3 | glucosamine derivative | 3.75 LU/ml | 6.2 | n.a. |
| EDC10 | poly-Arg derivative | 3.75 LU/ml | 4.5 | 2.7 |
| EDC11 | poly-Lys derivative | 3.75 LU/ml | 6.3 | 3.5 | n.a.: data not available

EXAMPLE 12

Washing performance of Lipolase and derivatives thereof of the invention

Swatches

Textile swatches containing fat with a dyestuff as an indicator for fat removal were prepared as follows: Bleached cotton (NT 2116 from Nordisk Tekstil) was cut into pieces of 3.5*3.5 cm. 0.075% (w/w) of Sudan red was added to lard at 70° C.; the mixture was kept at 5° C. and heated up to about 70° C. before use. 6 μl of the lard/Sudan red was applied to the centre of each swatch. The swatches were incubated at 70° C. for 30 minutes and kept overnight prior to the experiment. Two swatches were used for each experiment.

Conditions

The swatches were washed in glass beakers with agitation by a magnetic stirrer.
Volume: 100 ml
Detergent: European model detergent
Swatches: 6 swatches
pH: 10.2
Wash time: 20 min
Rinse: 15 min
Temperature: 30° C.
Drying: line drying
Repetitions: 3
Enzymes
Lipolase™
Lipolase™-glucosamine (EDC3), see example 7A and 11
Lipolase™-polylysine (EDC11), see example 7A and 11
Lipolase™-polyarginine (EDC10), see example 7A and 11
Evaluations The detergency of the enzymes was evaluated by measuring the remission at 460 nm (on a Elrepho-meter) on both sides of the swatches.

Delta R (remission) versus no enzyme.

|  | 300 LU/l | 750 LU/l | 1500 LU/l | 3000 LU/l | 10000 LU/l |
| --- | --- | --- | --- | --- | --- |
| Lipolase | 3.5 | 4.8 | 5.6 | 5.5 | 7.0 |
| EDC3 | 4.5 | 5.8 | 5.2 | 6.7 | 7.8 |
| EDC10 | 4.1 | 6.1 | 7.3 | 7.9 | 11.6 |
| EDC11 | 5.0 | 6.0 | 8.2 | 9.3 | 11.3 |

Further, Lipolase™ and the derivatives EDC10 and EDC11 were tested in a 3-cycle mini-wash assay under the following conditions:

Enzymes: 0, 300, 750, 1500, 3000, 10000 LU/1
Swatches/fabric: see above under swatches
Detergent: Heavy Duty Powder composition containing 1.17 g/l
Linear alkylbenzene sulphonate, 0.15 g/l AEO (Dobanol 25–7), 1.25 g/l sodium triphosphate, 1 g/l sodium sulphate, 0.45 g/l
sodium carbonate, 0.15 g/l sodium metasilicate; pH 10.2.

Wash: 6 swatches in 100 ml water per beaker were washed at 30° C. for 20 minutes, rinsed for 15 minutes in running tap water and dryed overnight at room conditions.

Evaluation: After each wash cycle the reflectance was measured on both sides of the swatches at 460 nm. The improvement factor IF was calculated as described in example 11.

The following results were obtained:

| Enzyme | IF |
| --- | --- |
| Lipolase™ | 1.0 |
| EDC10 | 1.5 |
| EDC11 | 2.6 |

EXAMPLE 13

Modified endo-xylanase (hemicellulase) for kraft pulp

Samples of oxygen bleached kraft pulp was repulped at 1.5% consistency in a laboratory pulper with 10.000 revolutions according to SCAN C18 and drained on a Buchner funnel. The pH was adjusted with sulfuric acid. The samples were diluted to 10% consistency. A purified endo-xylanase preparation obtained from *T.lanuginosus* was added to two pulp samples with pH 7 and 8.5 respectively, at a rate of 765 U/kg. One U is defined as the amount of endo-xylanase that in one minute hydrolyses one micromole of beta 1–4 linkages in a xylan polymer. To two other samples with pH 7 and 8.5 were added *T. lanuginosus* endo-xylanase modified according to the invention (see e.g. example 1D), also at a rate of 765 U/kg. Finally two control samples were adjusted in pH to respectively 7 and 8.5.

The 6 pulp samples were now incubated in closed plastic bags immersed in thermostated water at 60° C. The bags were kneaded by hand 30 seconds every 15 minutes. After three hours incubation time the pulp samples were drained. Samples of the waterphase were filtered through a 45 micrometer filter in order to remove any micro-fibrils from the pulp, and the final pH and the absorbance at 280 nm were determined. The pulp samples were then washed with deionized water, and the level of residual lignin was measured as kappa no. The results are given in the table below. In each figure the control value has been subtracted.

At pH 7, the effect of the treatment with the modified (derivatised) endo-xylanase is an increase of the amount of released lignin of factor 2.9 and, correspondingly, a decrease in the residual lignin level which is a reduction of the kappa number with a factor 2.9.

At the alkaline pH 8.5, the amount of released lignin is 460% higher when the modified endo-xylanase is used as compared to the unmodified reference enzyme. The decrease in kappa number is 12.6 times higher with the modified endo-xylanase as compared to the reference (the unmodified enzyme).

TABLE

|  | Final pH | Released lignin | Decrease in kappa no. |
|---|---|---|---|
| Reference pH 7 | 7.02 | 1.736 | 0.49 |
| Derivative pH 7 | 7.00 | 5.036 | 1.42 |
| Reference pH 8.5 | 8.36 | 0.854 | 0.08 |
| Derivative pH 8.5 | 8.37 | 3.890 | 1.01 |

The results show that the performance of an endo-xylanase is improved drastically, also in the alkaline pH range, when modified, i.e. derivatised, according to the present invention.

THE DRAWINGS

The invention is further illustated by the drawings in which

Figure 1:
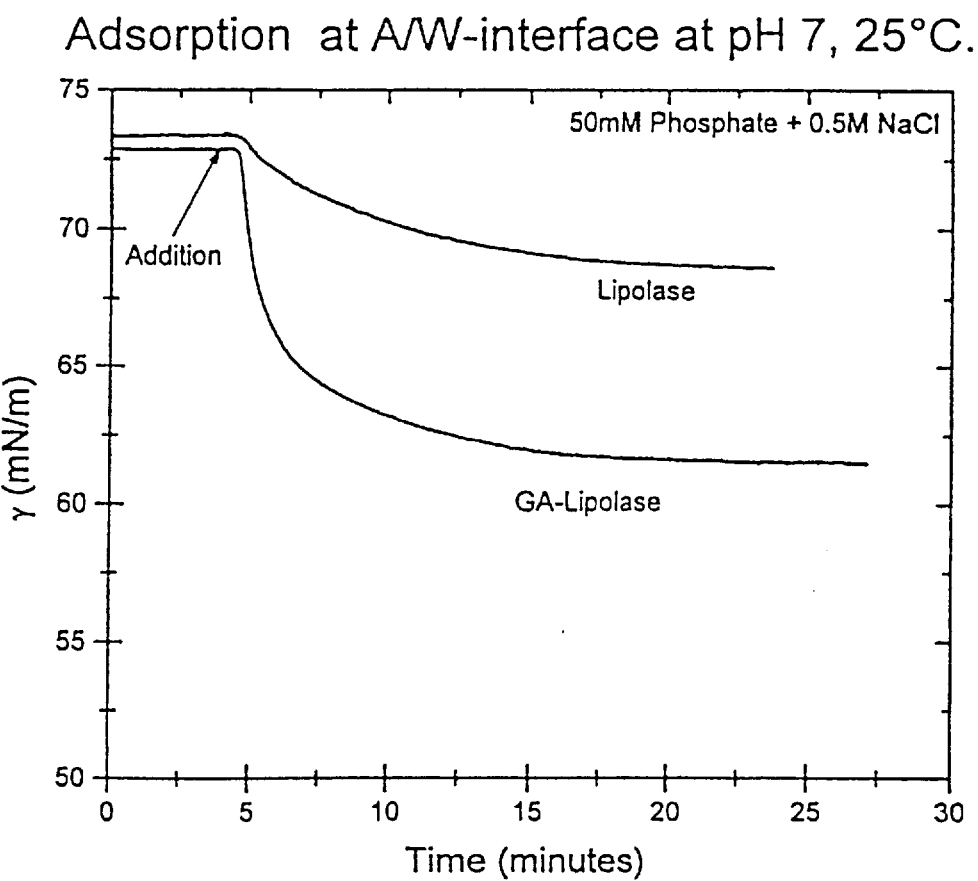
FIG. 1 shows the adsorption of Lipolase and GA-lipolase at A/W-interface at pH 7, 25° C.
Figure 2:
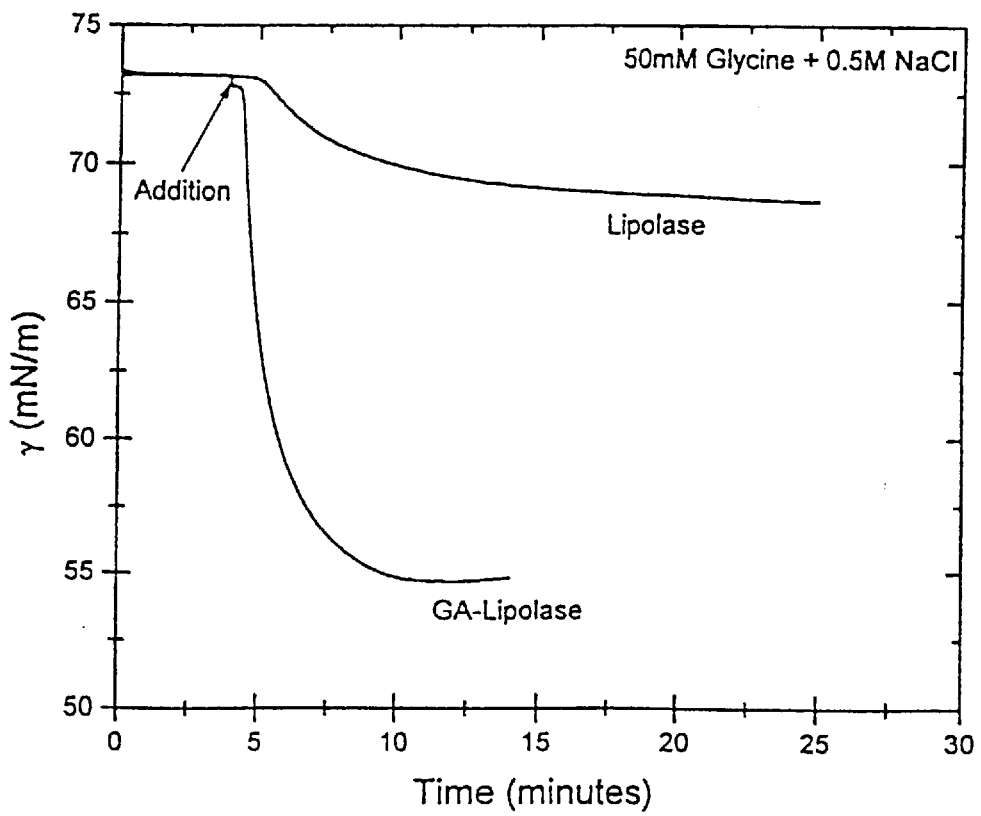
FIG. 2 shows the adsorption of Lipolase and GA-lipolase at A/W-interface at pH 10, 25° C.
Figure 3:
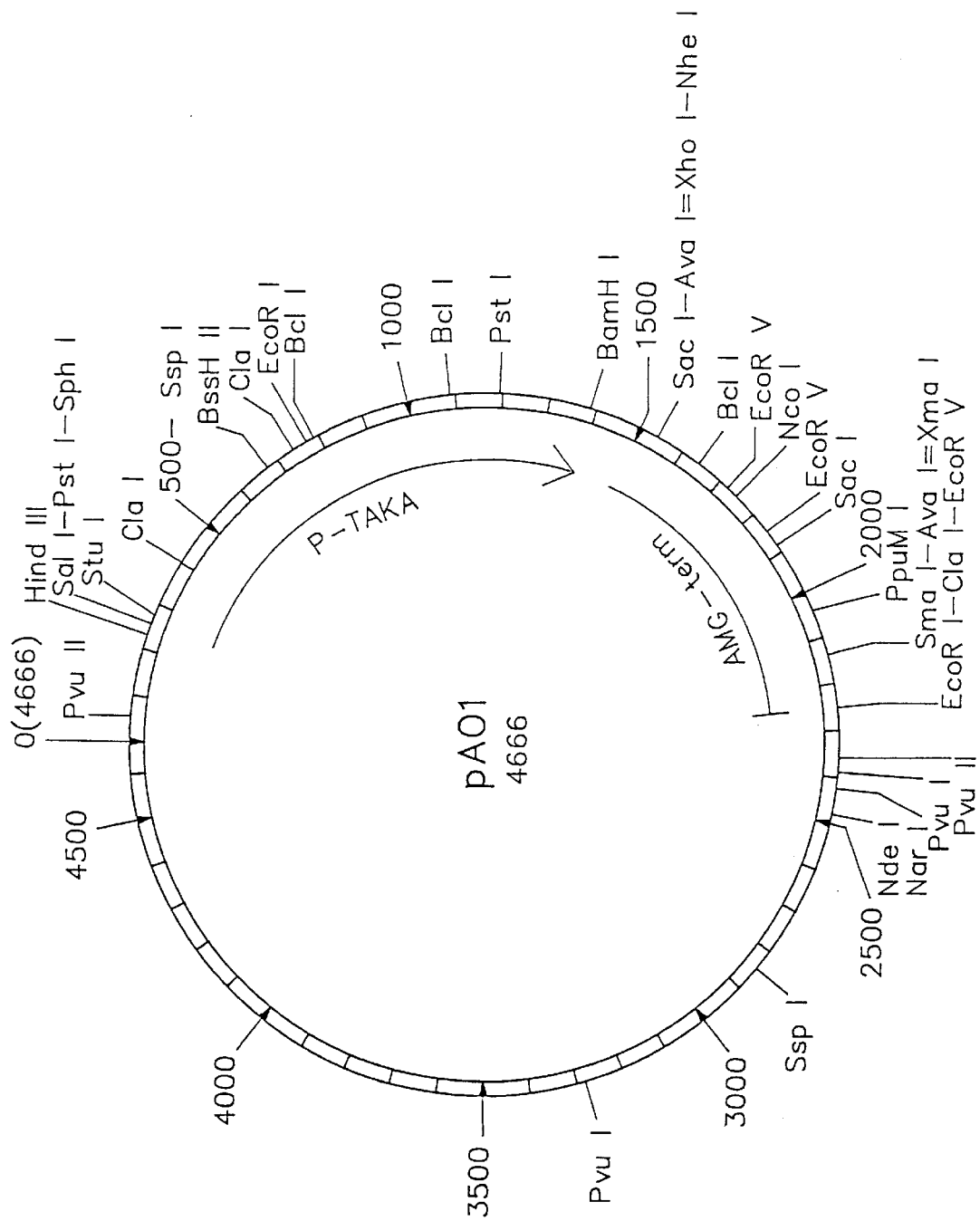
FIG. 3 shows the plasmide paO1.
Figure 4:
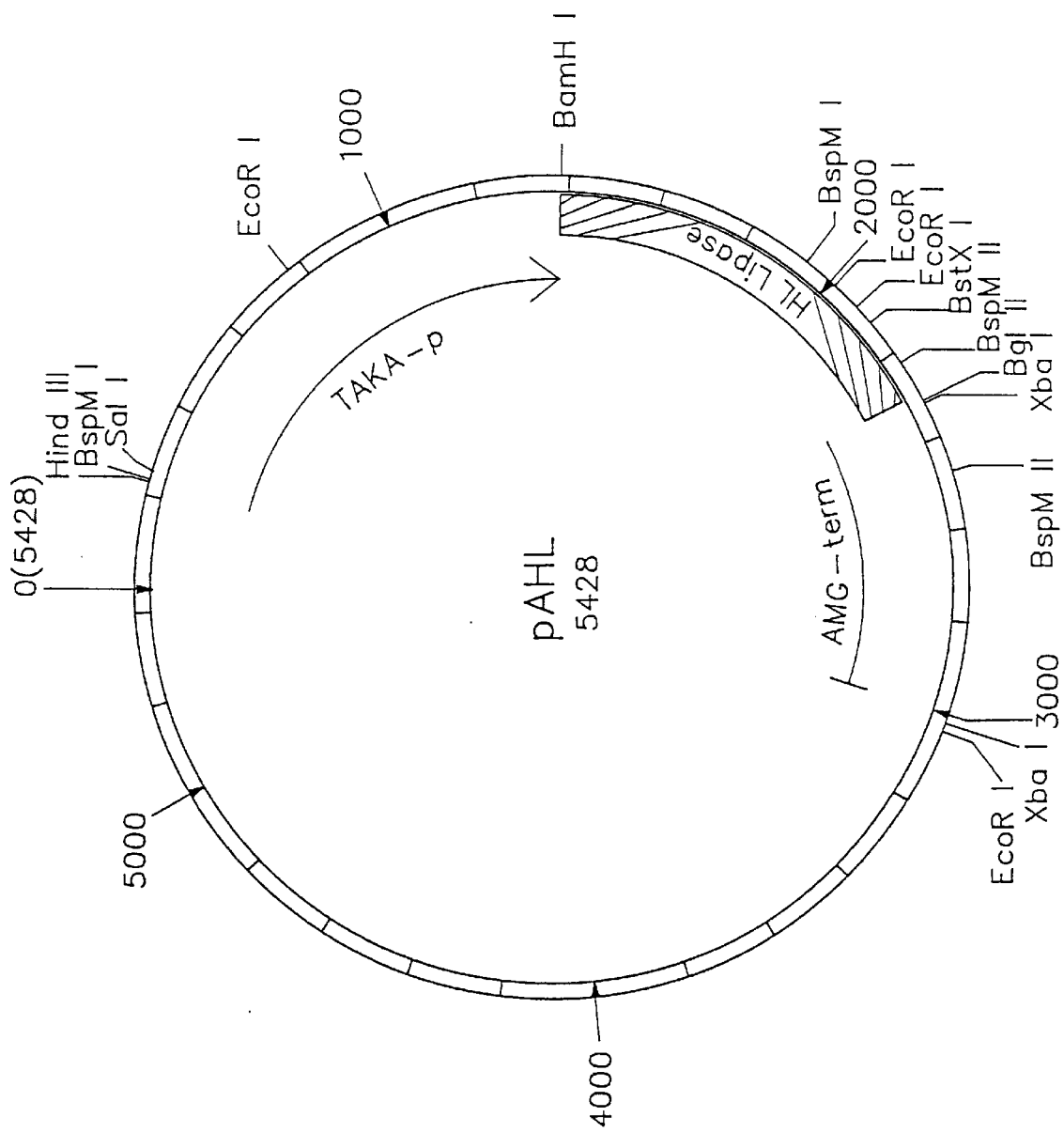
FIG. 4 shows the plasmide pAHL.
Figure 5:
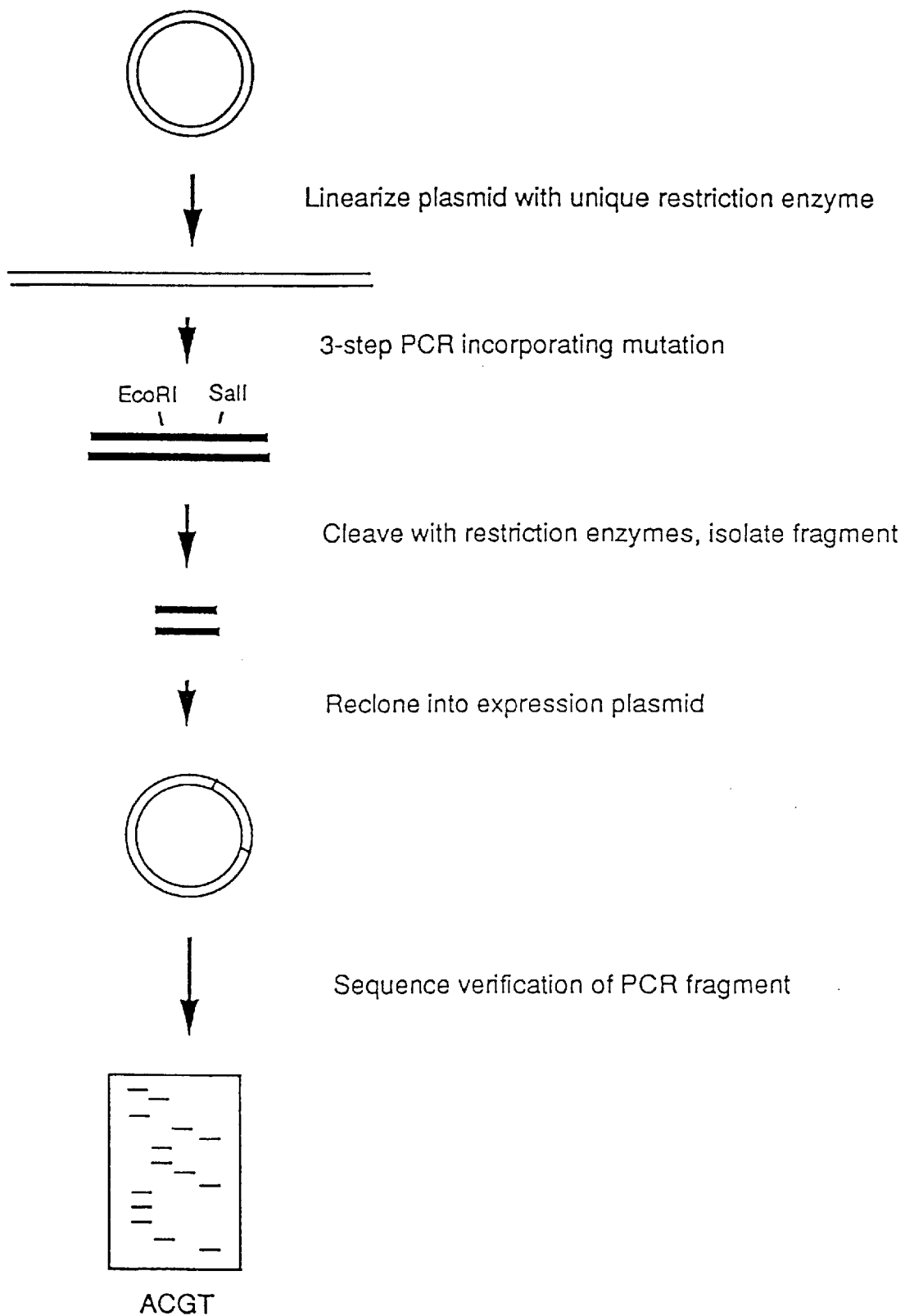
FIG. 5 and FIG. 6 illustrate the method of 3-step PCR mutagenesis.
Figure 6:
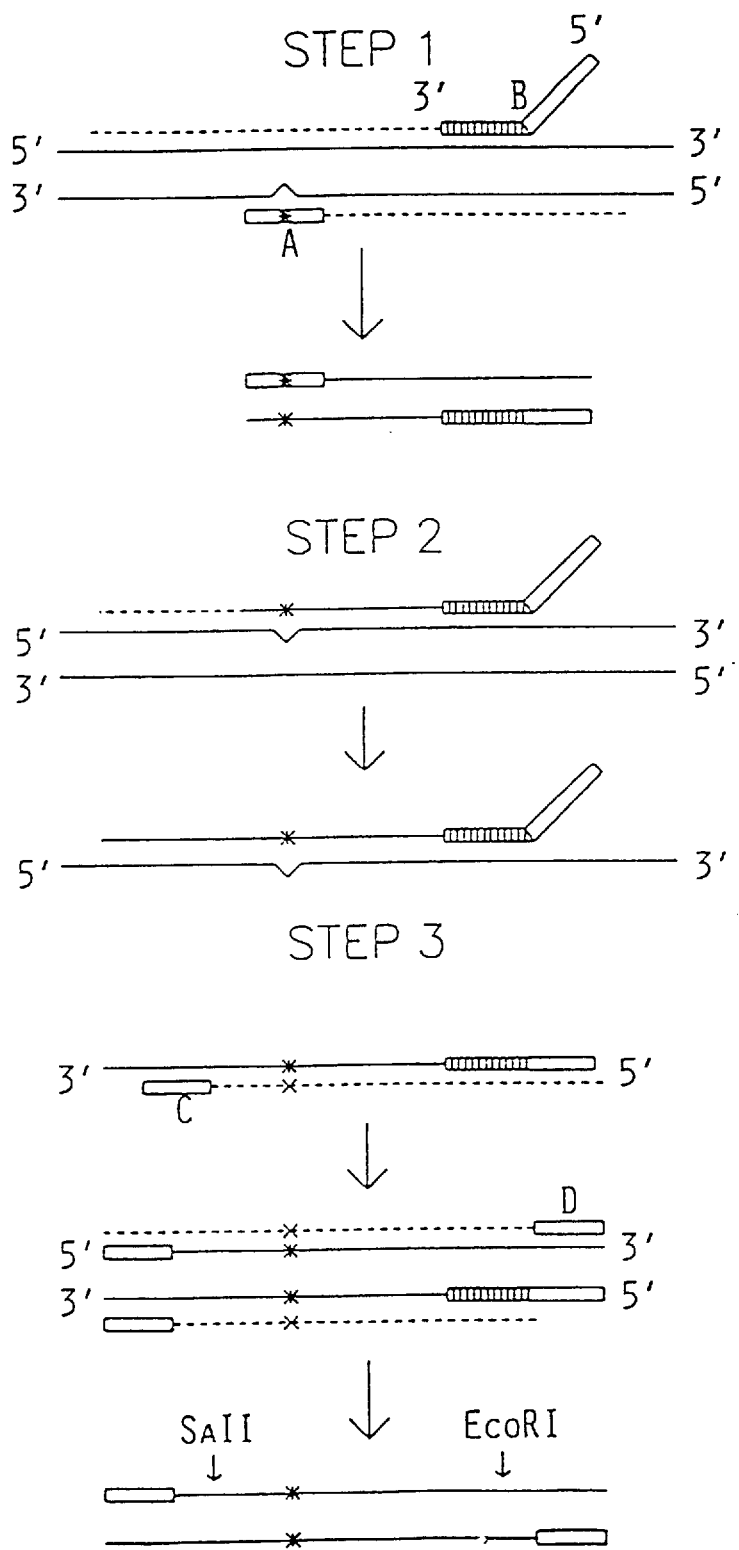

We claim:

1. An enzyme preparation comprising a modified enzyme, wherein the modification comprises coupling an amine group to the carboxyl group of a glutamic acid or aspartic acid residue, and wherein the enzyme is selected from the group consisting of an amylase, lipase, oxidoreductase, pectinase, and hemicellulase.

2. An enzyme preparation according to claim 1, wherein the pI of the modified enzyme is as least one pI unit higher than that of the parent enzyme.

3. An enzyme preparation according to claim 1 wherein the amine is an aminated sugar, aminated alkane, aminated alcohol, aminated polyalcohol or amino acid or an ester or other derivatives thereof.

4. An enzyme preparation according to claim 3, wherein the aminated sugar is glucosamine, isomeric forms thereof, or oligomers or polymers thereof.

5. An enzyme preparation according to claim 3, wherein the aminated alcohol having at least 3 carbon atoms, for instance aminopropanol or aminobutanol.

6. An enzyme preparation according to claim 3, wherein the aminated polyalcohol is D-glucamine, isomers thereof, or oligomers or polymers thereof.

7. An enzyme preparation according to claim 3, wherein the amino acid is lysine, spermine, spermidine, putrescine, or polymers thereof such as polylysine and polyarginine.

8. An enzyme preparation according to claim 1, wherein the coupling of the amine to the carboxyl group of glutamic acid or aspartic acid residues is mediated by a crosslinking agent capable of binding a carboxyl group and an amino group.

9. An enzyme preparation according to claim 8, wherein the crosslinking agent is selected from the group consisting of carbodiimides, isoxazolium derivatives, chloroformates or carbonyldiimidazole.

10. An enzyme preparation according to claim 9, wherein the crosslinking agent is a carbodiimide.

11. An enzyme preparation according to claim 1, wherein the pI of the modified enzyme is at least 8.0.

12. An enzyme preparation according to claim 11, wherein the pI of the modified enzyme is at least 8.5.

13. An enzyme preparation according to claim 12, wherein the pI of the modified enzyme is at least 9.0.

14. An enzyme preparation according to claim 2 wherein the pI of the modified enzyme is as least two pI units higher than that of the parent enzyme.

15. An enzyme preparation according to claim 14, wherein the pI of the modified enzyme is as least three pI units higher than that of the parent enzyme.

16. A detergent additive comprising an enzyme preparation according to claim 1 in the form of a non-dusting granulate, stabilized liquid or protected enzyme.

17. A detergent composition comprising an enzyme preparation according to claim 1 as well as a surfactant.

18. A detergent composition according to claim 17 wherein the enzyme preparation is present in a concentration corresponding to 0.01–100, preferably 0.05–60, mg of enzyme protein per liter of wash liquor.

19. A detergent composition according to claim 18 which is a dishwashing detergent.

20. A method for the treatment of lignocellulosic fibers, wherein the fibers are treated with an enzyme preparation according to claim 1, in an amount which is efficient for improving the fiber properties.

21. A method according to claim 20, wherein the enzyme preparation comprises a pectinase, a hemicellulase, an endo-xylanase, or a combination thereof.

22. A method according to claim 20 wherein the lignocellulosic fibers are kraft pulp which is treated with the enzyme preparation in an amount which is efficient for substantially lowering the content of residual ligning in the pulp.

23. A method according to claim 20 for enzymatic deinking of recycled paper pulp, wherein the enzyme preparation is applied in an amount which is efficient for effective deinking of the fibre surface.

* * * * *

UNITED STATES PATENT AND TRADEMARK OFFICE
CERTIFICATE OF CORRECTION

PATENT : 5,866,526
DATED : February 2, 1999
INVENTOR(S): Olsen et al.

It is certified that error appears in the above-identified patent and that said Letters Patent is hereby corrected as shown below:

On the title page, item [57]

In the Abstract, line 3, delete "oxidorcductase", and insert --oxidorecductase--.

In the Abstract, line 3, delete "pectinace" and insert --pectinase--.

Col. 9, line 25, delete "(amym)" and insert --(amyM)--.

Col. 9, line 52, delete "amds" and insert --amdS--.

Col. 12, line 36, delete "C45" and insert --$C_{4-5}$--.

Col. 13, line 53, delete "yes" and insert --dyes--.

Col. 19, line 25, delete "amds" and insert --amdS--.

Col. 19, line 49, delete "amds" and insert --amdS--.

Col. 21, line 43, delete "glucosamination" and insert --glucosamine--.

UNITED STATES PATENT AND TRADEMARK OFFICE
CERTIFICATE OF CORRECTION

PATENT : 5,866,526
DATED : February 2, 1999
INVENTOR(S): Olsen et al.

It is certified that error appears in the above-identified patent and that said Letters Patent is hereby corrected as shown below:

Col. 27, line 26, delete "paO1" and insert --pAO1--.

Col. 28, line 46, Claim 22, delete "ligning" and insert --lignin--

Signed and Sealed this

Twenty-third Day of November, 1999

Attest:

Attesting Officer

Q. TODD DICKINSON

Acting Commissioner of Patents and Trademarks